(12) United States Patent
Okada

(10) Patent No.: US 8,663,221 B2
(45) Date of Patent: Mar. 4, 2014

(54) ENDOSCOPIC TREATMENT TOOL

(75) Inventor: Tsutomu Okada, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1164 days.

(21) Appl. No.: 11/811,044

(22) Filed: Jun. 8, 2007

(65) Prior Publication Data
US 2008/0306334 A1    Dec. 11, 2008

(51) Int. Cl.
*A61B 18/14* (2006.01)

(52) U.S. Cl.
USPC ............................................................ 606/45

(58) Field of Classification Search
USPC ............... 600/104, 128, 139, 144; 604/95.04; 606/32–52, 170, 205–207
See application file for complete search history.

(56) References Cited

U.S. PATENT DOCUMENTS

| | | | |
|---|---|---|---|
| 4,708,137 A * | 11/1987 | Tsukagoshi | 606/46 |
| 4,977,887 A * | 12/1990 | Gouda | 600/144 |
| 5,125,395 A * | 6/1992 | Adair | 600/121 |
| 5,378,234 A * | 1/1995 | Hammerslag et al. | 604/95.04 |
| 5,441,499 A * | 8/1995 | Fritzsch | 606/45 |
| 5,762,615 A * | 6/1998 | Weier | 600/585 |
| 5,766,184 A * | 6/1998 | Matsuno et al. | 606/142 |
| 6,530,897 B2 * | 3/2003 | Nardeo | 604/95.04 |
| 6,602,207 B1 * | 8/2003 | Mam et al. | 600/585 |
| 6,790,173 B2 * | 9/2004 | Saadat et al. | 600/114 |
| 6,893,440 B2 * | 5/2005 | Durgin et al. | 606/45 |
| 7,837,620 B2 * | 11/2010 | Nobis et al. | 600/142 |
| 2003/0074014 A1 * | 4/2003 | Castaneda | 606/167 |
| 2003/0109778 A1 * | 6/2003 | Rashidi | 600/374 |
| 2004/0210284 A1 * | 10/2004 | Okada | 607/96 |
| 2005/0131457 A1 * | 6/2005 | Douglas et al. | 606/205 |
| 2006/0041254 A1 * | 2/2006 | Francischelli et al. | 606/41 |
| 2006/0106447 A1 * | 5/2006 | Opolski | 623/1.11 |
| 2006/0276784 A1 | 12/2006 | Miyajima et al. | |
| 2007/0088354 A1 * | 4/2007 | Sugita | 606/46 |
| 2007/0149852 A1 * | 6/2007 | Noguchi et al. | 600/144 |
| 2009/0124857 A1 * | 5/2009 | Viola | 600/141 |

FOREIGN PATENT DOCUMENTS

| | | |
|---|---|---|
| JP | 62-50610 | 3/1987 |
| JP | 8-299355 | 11/1996 |
| JP | 2002-291688 A | 10/2002 |
| JP | 2004-65745 A | 3/2004 |

(Continued)

OTHER PUBLICATIONS

Extended European Search Report dated May 3, 2011.

(Continued)

*Primary Examiner* — Ronald Hupczey, Jr.
(74) *Attorney, Agent, or Firm* — Scully, Scott, Murphy & Presser, P.C.

(57) ABSTRACT

An endoscopic treatment tool includes a flexible sheath; an operating member inserted to the sheath so as to freely advance and retract; a treatment section disposed at the distal end of the operating member that protrudes and retracts from the sheath; and an operator section connected to the proximal end of the operating member including a sliding member which makes the operating member advance and retract. The endoscopic treatment tool includes the operating member consisting of a member which increases its rigidity by compression, and a member which compresses the operating member. Therefore a sufficient incision or excision is achieved relative to the distance of movement of the treatment tool by preventing a deflection of the flexible tube when in use.

11 Claims, 8 Drawing Sheets

(56) References Cited

FOREIGN PATENT DOCUMENTS

| | | |
|---|---|---|
| JP | 2004-261372 | 9/2004 |
| JP | 2005-230080 | 9/2005 |
| WO | 97/12557 | 4/1997 |
| WO | 2004/110294 A1 | 12/2004 |

OTHER PUBLICATIONS

Notice of Reasons for Rejection dated Dec. 11, 2012 from corresponding Japanese Patent Application No. 2008-131277 together with an English language translation.

* cited by examiner

ENDOSCOPIC TREATMENT TOOL

BACKGROUND OF THE INVENTION

1. Field of the Invention

The present invention relates to endoscopic treatment tools, in particular to treatment tools such as a high-frequency knife for incising biological tissue.

2. Description of the Related Art

Conventionally, a treatment procedure for incising biological tissue such as a mucous membrane has been conducted endoscopically. In such an incision procedure, a high-frequency treatment tool disclosed in such as Japanese Unexamined Utility Model Application, Publication No. S62-50610 is used.

The high-frequency treatment tool such as disclosed in the above document and Japanese Patent Application, First Publication No. Hei 8-299355, and Japanese Patent Application, First Publication No. 2005-230080, include a needle-like electrode (treatment section) which extends to an axial direction disposed at a distal end of an operating wire inserted through a flexible sheath. Biological tissue which is in contact with the electrode knife will be cauterized to incise by transmitting a high-frequency current through the knife.

Tubes and coils may be used for the flexible tube and wires and coils may be used for the operating wire. Thus, flexibility is maintained upon combining the tube and the wire.

However, when incision and excision of tissue is performed with the high-frequency treatment tool disclosed in Japanese Unexamined Utility Model Application, Publication No. S62-50610, a knife 102 of the high-frequency treatment tool 101 disposed at the distal end of an endoscope 100 is pierced to an incision target site A, then incision and excision is performed by moving the knife along the pre-determined incision direction B, such as shown in FIG. 14A.

At this time, backward deflection to the direction of movement of a sheath 103 occurs after the treatment tool is moved due to the flexibility of the sheath 103 of the high-frequency treatment tool 101, hence there have often been problems of insufficient incision and excision relative to the distance of movement of the treatment tool.

Even the treatment tools provided with a tightly wound coil as the flexible tube or the operating wire such as those disclosed in Japanese Patent Application, First Publication No. 8-299355 and Japanese Patent Application, First Publication No. 2005-230080 have the same problems due to the flexibility of the tightly wound coil.

The present invention was conceived in view of the above-described circumstances and has as its objective the provision of an endoscopic treatment tool with which the treatment section is protruded from a flexible pipe-like tube and to prevent deflection of the flexible tube when in use so that a sufficient incision and excision is achieved relative to the distance of the movement of the treatment tool.

SUMMARY OF THE INVENTION

An endoscopic treatment tool according to the present invention includes a flexible sheath; an operating member inserted to the sheath so as to freely advance and retract; a treatment section disposed at the distal end of the operating member that protrudes and retracts from the sheath; and an operator section connected to the proximal end of the operating member including a sliding member which makes the operating member advance and retract. The endoscopic treatment tool according to the present invention includes the operating member consisting of a member which increases the rigidity by compression and a member which compresses the operating member.

By providing the structure above, when the treatment section is made to protrude from the distal end of the sheath to perform an operation such as incision or excision by moving around the target site, a deflection can be prevented by increasing the rigidity of the sheath by compressing the operating member. Therefore a sufficient incision or excision and so on can be achieved relative to the distance of movement of the treatment tool.

Furthermore, it is preferable to include a member which maintains a compressed status of the operating member which has been achieved by the member which compresses the operating member.

Furthermore, as for the member which increases the rigidity by compression, a spring may be used, for example.

Furthermore, it is also preferable to include an abutting member at the distal end of the sheath, where the treatment section can be inserted and the distal end of the operating member comes into contact so that the abutting member is unable to penetrate through.

Furthermore, the member which compresses the operating member may be disposed at the operator section. In this case, the member which compresses the operating member may be the sliding member of the operator section.

Furthermore, the member which maintains a compressed status of the operating member may be disposed at the operator section. In this case, the member which maintains the compressed status of the operating member may be a member which prevents the sliding member of the operator section from retracting.

Furthermore, as for the endoscopic treatment tool, such as a high-frequency knife in which the treatment section is an electrode may be used.

DETAILED DESCRIPTION OF THE INVENTION

First Embodiment

A first embodiment of the present invention will be explained with reference to FIGS. 1 and 2.

Figure 1:
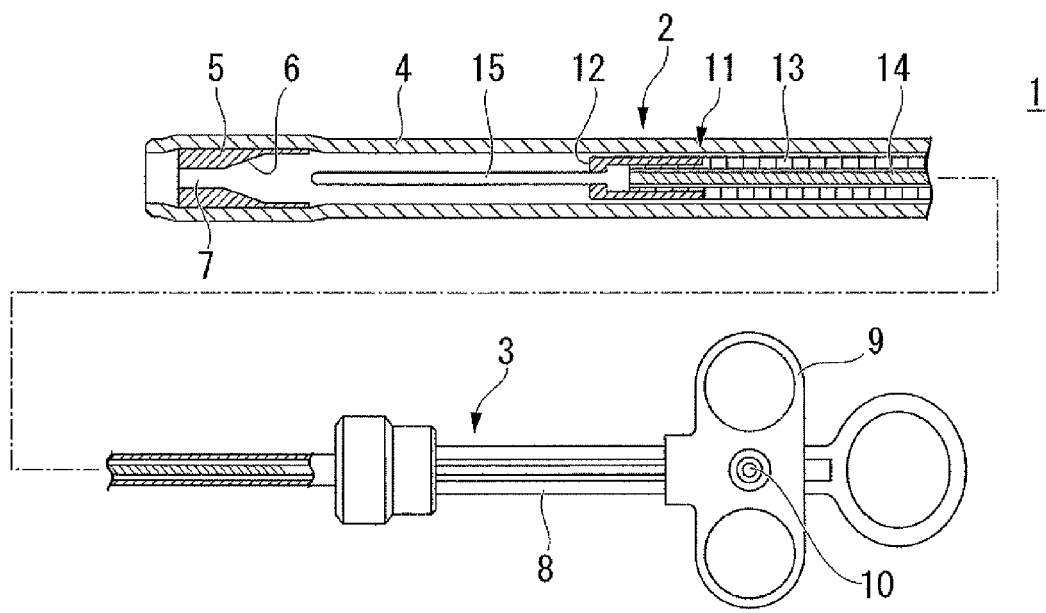
FIG. 1 is a partial cross-sectional view of a structure of the high-frequency knife of a first embodiment of the present invention, showing a state where the electrode knife is pulled inside of the sheath.

As shown in FIG. 1, a high-frequency knife (endoscopic treatment tool) 1 according to the present embodiment includes a flexible sheath 2 which can be inserted to an endoscopic channel (not shown) as a main body, and an operator section 3 disposed at the proximal end of the sheath 2. The sheath 2 includes an insulating tube 4, for instance made of tetrafluoroethylene and so on.

A pipe-like stopper member (abutting member) 5 is disposed at the distal end of the sheath 2 and an outer periphery of the stopper 5 is covered with the distal portion of the insulating tube 4. The inner surface of the stopper 5 has a tapered portion 6 with a reduced diameter toward the distal side, and a small diameter hole 7 is formed at the distal side of the tapered portion 6.

The operator section 3 of the high-frequency knife 1 includes an operator main body 8 and an operating slider 9 which freely advances and retracts with respect to the operator main body 8. The operating slider 9 has a connector 10 which is electrically connected to an unshown cord which leads to a high-frequency generator (not shown).

An electrically conductive operating member 11 is passed through the inside of the sheath 2 and the proximal end portion thereof is connected to the operating slider 9. On the other hand, the distal end portion of the operating member 11 is fitted with a stopper receiver 12 which is abutted to the tapered portion 6 of the stopper member 5. The operating member 11 has a structure in which a current transmitting wire 14 is inserted to a member which increases its hardness upon compression, such as a coil sheath 13.

A rod-shaped electrode knife (electrode section) 15 as the treatment section is connected to the stopper receiver 12 fitted at the distal end of the operating member 11. The electrode knife 15 is protruded to the axial direction from the distal end of the sheath 2. The electrode knife 15 is made of electrically conductive material and is electrically connected to the stopper receiver 12.

Therefore, the electrode knife 15 is electrically connected to the connector 10 of the operating slider 9 via the stopper receiver 12 and the operating member 11 and can be protruded and retracted from the distal portion of the sheath 2 via the small diameter hole 7 of the stopper member 5 by advancing and retracting the operating member 11.

The protrusion amount of the electrode knife 15 from the distal end of the sheath 2 is maintained uniformly by means of the stopper receiver 12 coming into contact with the tapered portion 6 of the stopper member 5. Furthermore, the coil sheath 13 can be compressed by advancing the operating slider 9 at the position where the stopper receiver 12 comes into contact with the tapered section 6 of the stopper member 5.

Next, operation using the high-frequency knife 1 of the present embodiment shall now be described referring to an endoscopic incision of a mucous membrane in the body cavity as shown by FIGS. 1 to 4.

As shown in FIG. 1, the operating slider 9 is retracted backward (to the proximal side) with respect to the operator main body 8 and the operating member 11 is retracted so that the electrode knife 15 is pulled in the sheath 2. At this position, the high-frequency knife 1 is inserted to a body cavity via a channel of the endoscope 16. Next, as shown in FIG. 2, when the operating slider 9 is made to advance forward (to the distal side) with respect to the operator main body 8, the operating member 11 is advanced forward and the stopper receiver 12 is stopped by abutting the tapered section 6 of the stopper member 5. Accordingly, the electrode knife 15 is protruded to the outside from the distal end of the sheath 2.

Figure 2:
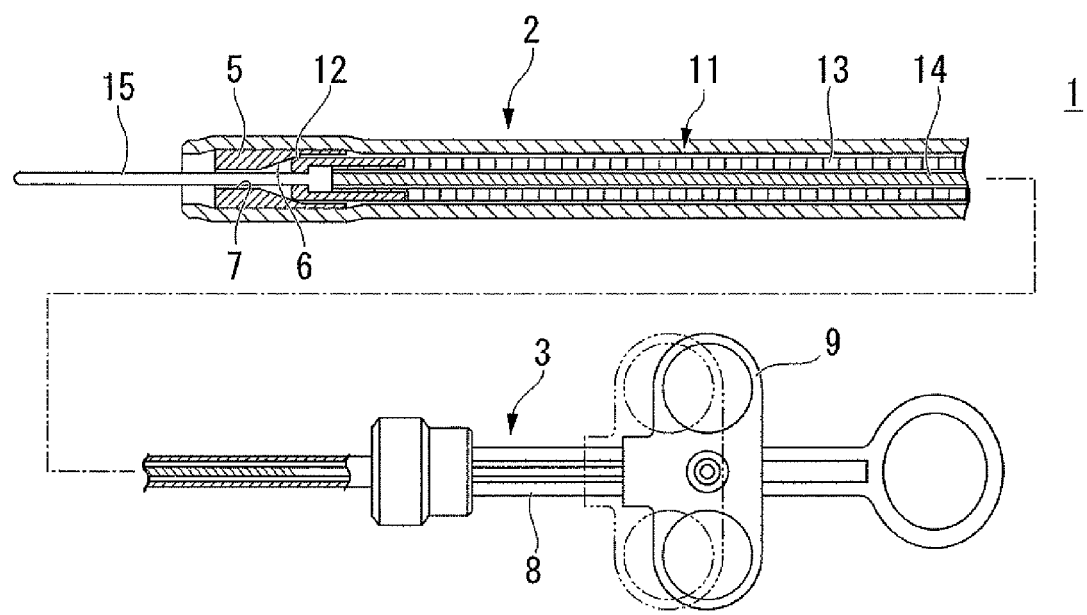
FIG. 2 is a partial cross-sectional view of a structure of the high-frequency knife of the first embodiment of the present invention, showing a state where the electrode knife is protruded from the distal end of the sheath.
Figure 3:
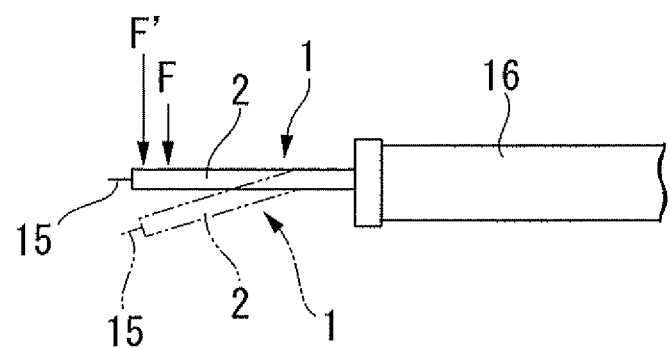
FIG. 3 is a view for describing the amounts of force exerted to the sheath from a side direction in order to deflect the sheath.

At this position, as shown by a dot-dash-line of FIG. 2, the operating slider 9 is further advanced with respect to the operator main body 8. Consequently, the operating member 11 is compressed and the coil sheath 13 is hardened and then, the sheath 2 also becomes compressed from a non-compressed state, thus preventing deflection. In other words, for instance, a force F exerted from a side direction to the sheath 2 in order to deflect the sheath 2 from a position shown in a straight line to a position shown in a dotted line in FIG. 3 increases as F to F' (given that F<F') along with a transfer from a non-compressed to a compressed state.

Figure 4:
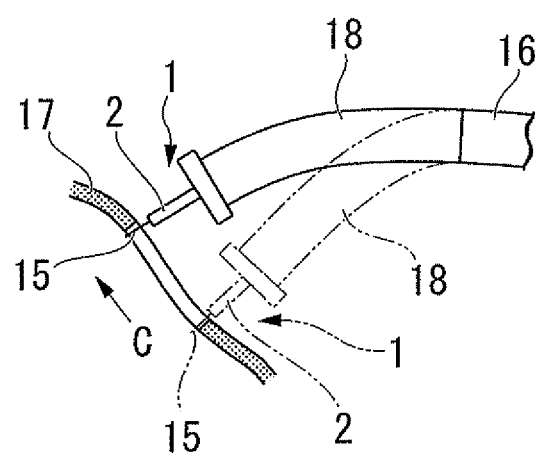
FIG. 4 is a view for describing a state of incising a mucous membrane using the high-frequency knife of the present invention.

Furthermore, as shown in FIG. 4, a mucous membrane 17 is incised by moving a curved portion 18 of the endoscope 16 for example to the direction shown by arrow C, while transmitting current to the electrode knife 15 at a position where the electrode knife 15 is pressed against the mucous membrane 17.

In the present embodiment, the operating member 11 consisting of the sheath 2 has the coil sheath 13 which can be hardened by compression, and hardening the coil sheath 13 can be achieved by operation of the operator section 3. Accordingly, when the electrode knife 15 is protruded from the distal end of the sheath 2 and used for incising while moving around the operation site, the deflection of the protruded portion from the distal end of the endoscope 16 can be prevented by hardening the sheath 2, and a sufficient incising can be achieved relative to the distance of movement.

Note that at the position shown in FIG. 2, since the stopper receiver 12 is in contact with the tapered portion 6 of the stopper member 5 from the proximal side, the current transmitting wire 14 is no longer further advanced. Accordingly, when the operating slider 9 is further advanced with respect to the operator main body 8 as shown by the dot-dash-line, and the coil sheath 13 is compressed, a deflection by the compressed amount of the coil sheath 13 is generated in the current transmitting wire 14. This deflection is absorbed into a space provided between an inner periphery of the coil sheath 13 and an outer periphery of the current transmitting wire 14.

Second Embodiment

Figure 5:
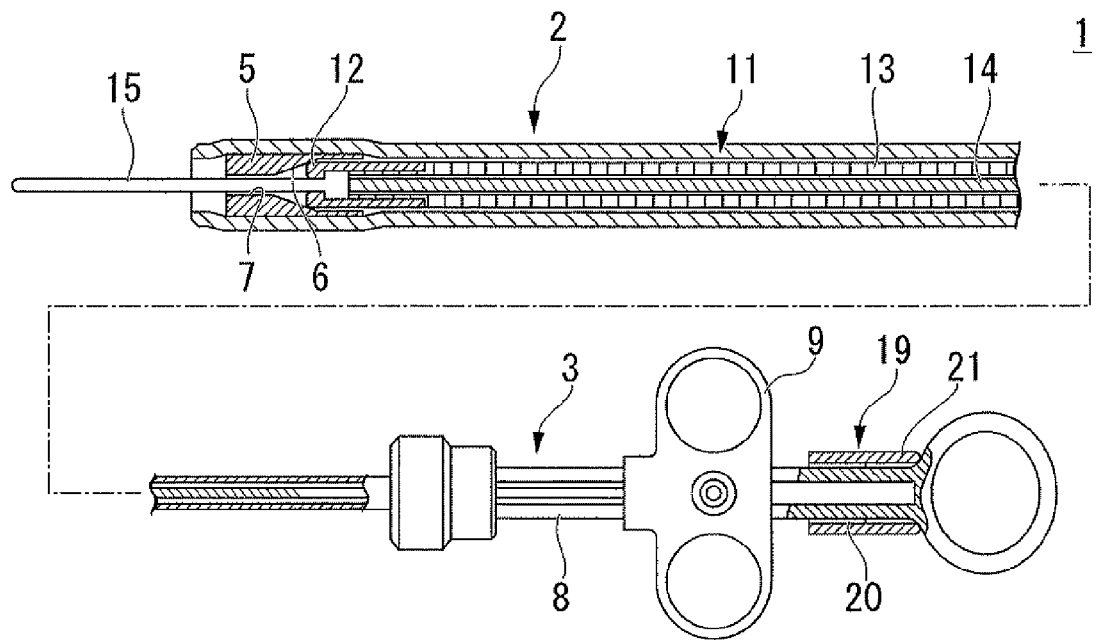
FIG. 5 is a partial cross-sectional view of a structure of the high-frequency knife of a second embodiment of the present invention, showing a state where the electrode knife is protruded from the distal end of the sheath.
Figure 6:
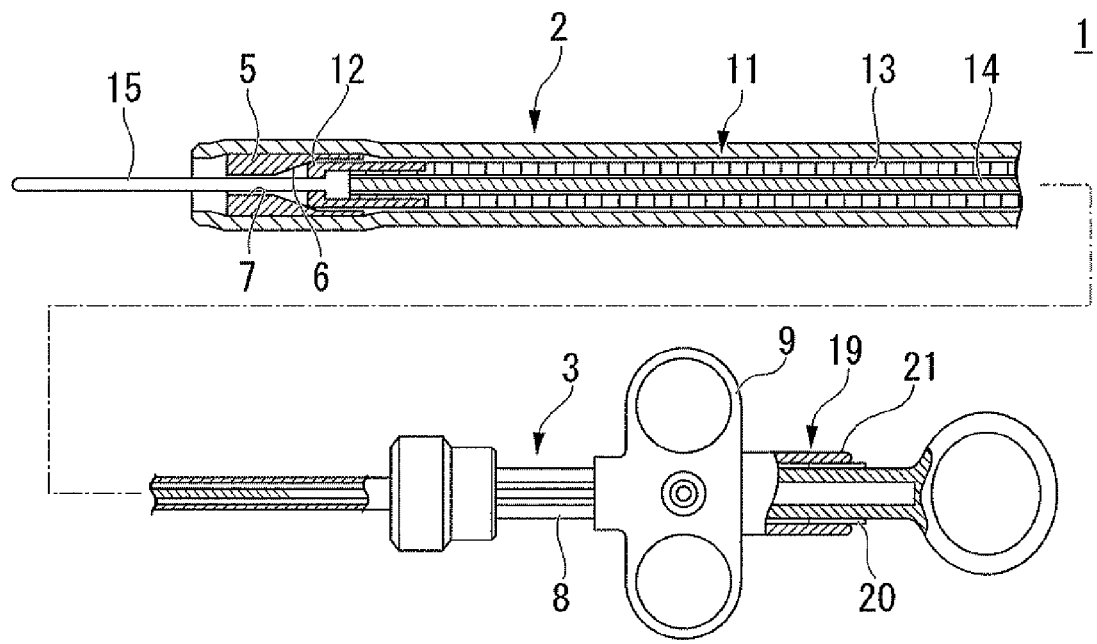
FIG. 6 is a partial cross-sectional view of a structure of the high-frequency knife of the second embodiment of the present invention, showing a state in which the operating member is further compressed from the position at FIG. 5.

FIGS. 5 and 6 show a second embodiment of the present invention.

In the high-frequency knife 1 of the present embodiment, the operator section 3 is provided with a holding member 19 which prevents retraction of the operating slider 9 and holds the electrode knife 15 at a protruded position. The holding member 19 includes an external thread 20 disposed on the operator main body 8 at the rear end of the operating slider 9 and a mobile member 21 engages therewith. The second embodiment differs from the first embodiment at this point.

Furthermore, the operation of the present embodiment differs from the first embodiment by means of operating the holding member 19. That is, the mobile member 21 is advanced by rotating the mobile member 21 relative to the external thread 20 from the position where the electrode knife 15 is protruded from the distal end of the sheath 2 (refer to FIG. 5).

The operating member 11 is then compressed and the operating slider 9 is made to advance with respect to the operator main body 8 till the coil sheath 13 is hardened. Simultaneously, as shown in FIG. 6, the retraction of the operating slider 9 is prevented. Apart from this action, other actions are the same as the first embodiment.

In this embodiment, since there is no need to keep holding the operating slider 9 in order to maintain the compressed status of the operating member 11, an operator can release his/her hands from the operating slider 9 while the operating member 11 is being compressed.

Third Embodiment

Figure 7:
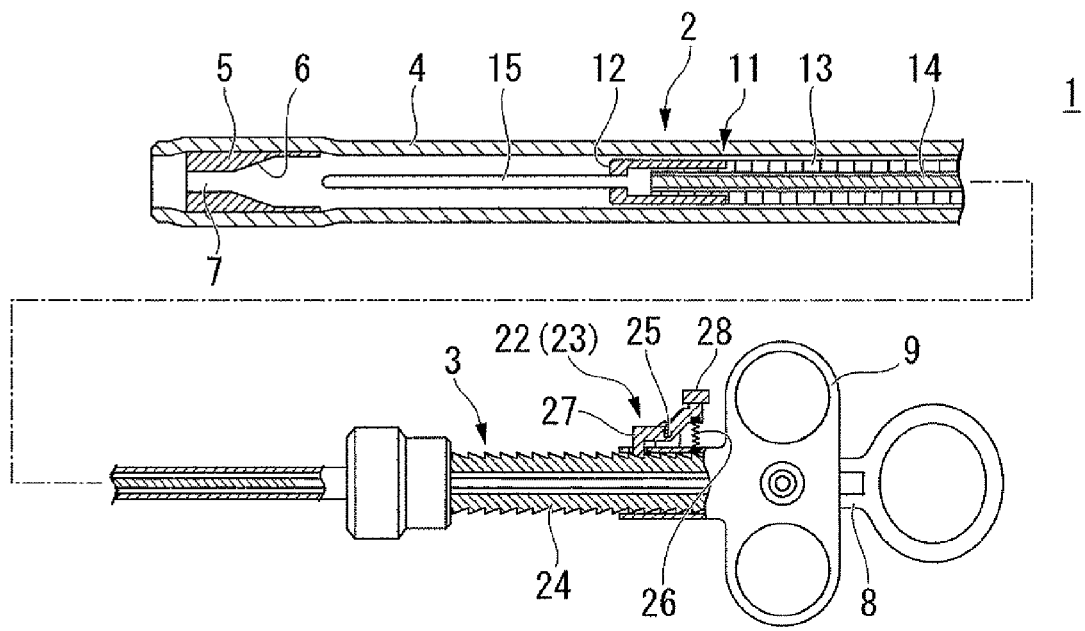
FIG. 7 is a partial cross-sectional view of a structure of the high-frequency knife of a third embodiment of the present invention, showing a state where the electrode knife is pulled inside of the sheath.
Figure 8:
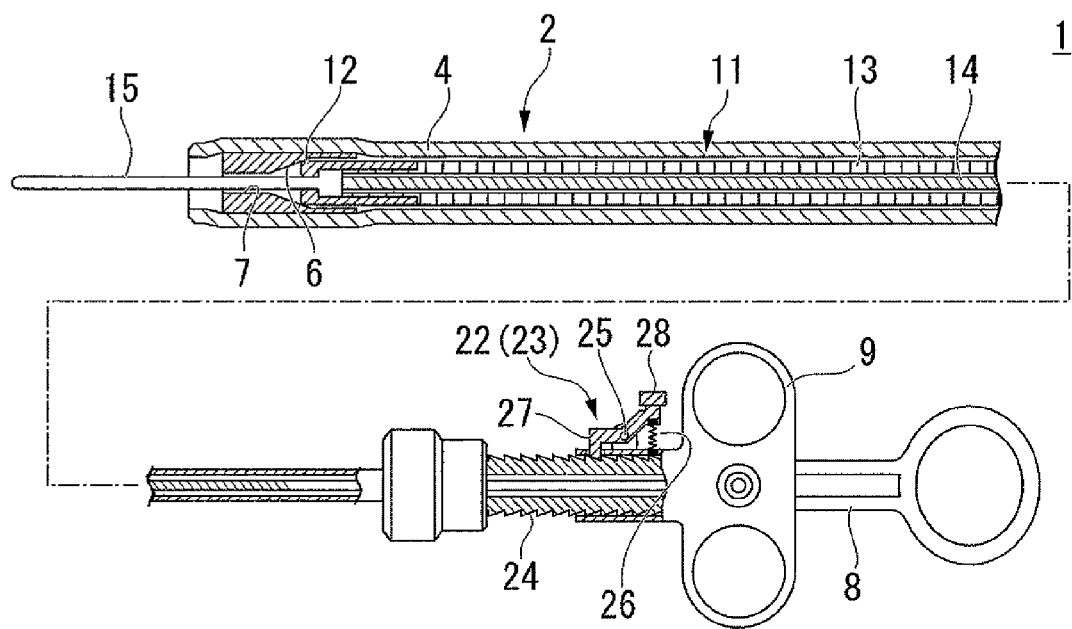
FIG. 8 is a partial cross-sectional view of the structure of the high-frequency knife of the third embodiment of the present invention, showing a state where the electrode knife is protruded from the distal end of the sheath.
Figure 9:
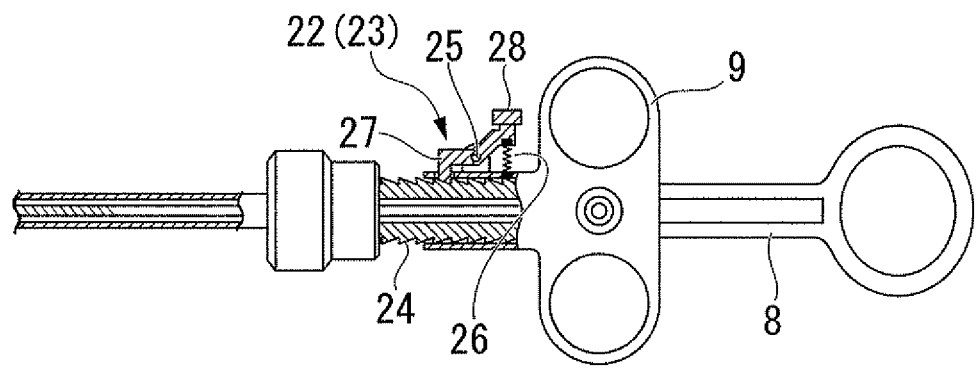
FIG. 9 is a partial cross-sectional view of the operator section of the high-frequency knife of the third embodiment of the present invention, showing a state in which the operating member is further compressed from the position at FIG. 8.

FIGS. 7 to 9 show a third embodiment of the present invention.

In the high-frequency knife 1 of the present embodiment, the operator section 3 is provided with a ratchet device 23 which prevents the operating slider 9 from retracting and holds the electrode knife 15 at the protruded position as by means a holding member 22. The ratchet device 23 includes a plurality of slanting teeth 24 disposed on the distal side of the operator main body 8 with respect to the operating slider 9, and a pawl 27 which is pivotally mounted at the distal end of the operating slider 9 by a pin 25 and is spring-biased by a spring 26 toward the direction of clutching with the slanting teeth 24. The third embodiment differs from the first embodiment at this point.

Furthermore, the operation of the third embodiment differs from the first embodiment by means of operating the ratchet device 23. In particular, when the operating slider 9 is advanced, the pawl 27 of the ratchet device 23 crosses over the slanting teeth 24 opposed against the force of the spring 26, preventing the operating slider 9 from retracting at a stopped position. When the operating slider 9 is further advanced with respect to the operator main body 8 from the position where the electrode knife 15 is protruded from the distal end of the sheath 2 (refers to FIG. 8), the coil sheath 13 becomes hardened since the operating member 11 is compressed. At this stage, the advancement of the operating slider 9 is stopped and the operating slider 9 is fixed by maintaining the compressed status of the operating member 11 as shown in FIG. 9, so as to prevent the operating slider 9 from retracting. When the operating slider 9 is retracted by releasing the ratchet device 23, a button 28 disposed at the proximal end of the pawl 27 is pressed so that the clutch between the pawl 27 and the button 28 is released. Other operations are the same as the first embodiment.

In this embodiment, since it is also not required to keep holding the operating slider 9 in order to maintain the compressed status of the operating member 11, an operator can release his/her hands from the operating slider 9 while the operating member 11 is being compressed. Moreover, the steps from the protrusion of the electrode knife 15 to the compression of the operating member 11 and fixing the operating slider 9 can be performed with one sequential operation of shifting the operating slider 9.

Fourth Embodiment

FIGS. 10 to 13 show a fourth embodiment of the present invention.

In the high-frequency knife 1 of the present embodiment, structures of an operating member 29 and an electrode knife 30 differs from the other embodiments. The operating member 29 of the present embodiment includes an operating wire 31 and a coil sheath 32 disposed on the distal end of the operating wire 31. Here, the proximal portion of the coil sheath 32 is fixed at the proximal end of the operating wire 31 by a method such as brazing. Furthermore, as shown in FIG. 1, the length L from the distal end of the sheath 2 to the proximal end of the coil sheath 32 at a position where the electrode knife 30 is extruded from the sheath 2 is longer than the length l which is the length of the sheath 2 when extruded from the distal end of the endoscope 16 when in use, and shorter than the length l' which is the length from the distal end of the protruded sheath 2 to the proximal end 18a of a the curved portion 18 in the endoscope 16.

Furthermore, the electrode knife 30 includes a rod-shaped electrode portion 30a which is protruded from the proximal end of sheath 2 to the axial direction, and an articulated portion 30b where the proximal end of the rod-shaped electrode portion 30a is articulated substantially by an angle of 90 degrees.

Figure 10:
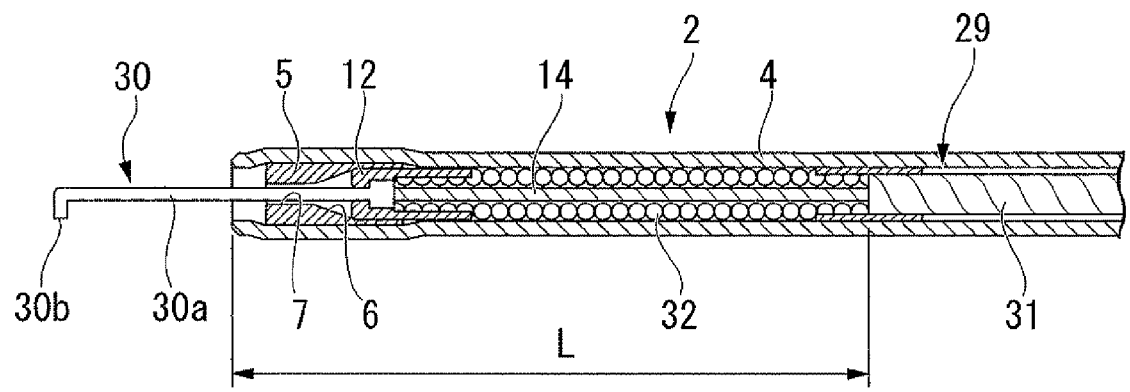
FIG. 10 is a partial cross-sectional view of the distal end portion of the high-frequency knife as an example of a structure of the high-frequency knife of a fourth embodiment of the present invention, showing a state where the electrode knife is protruded from the distal end of the sheath.
Figure 11:
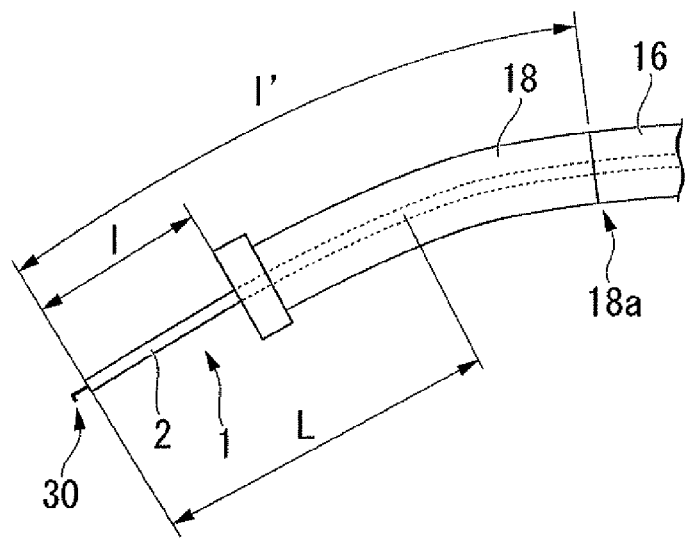
FIG. 11 is a view showing the distal end portion of the endoscope which is fitted by the high-frequency knife of the fourth embodiment of the present invention.
Figure 12:
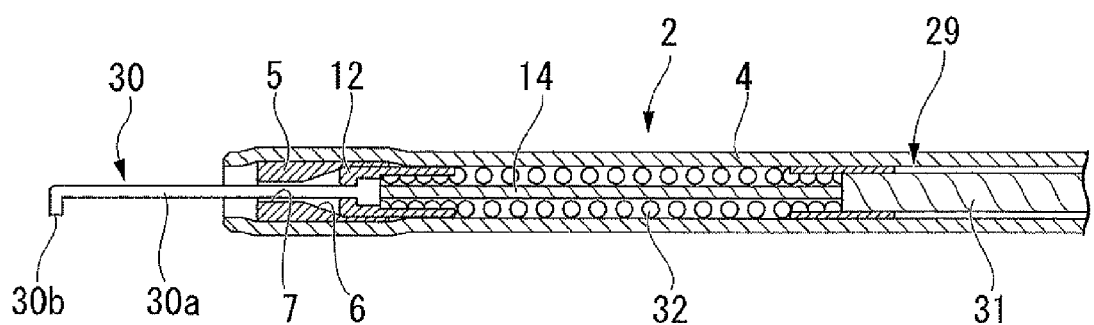
FIG. 12 is a partial cross-sectional view of the distal end portion of the high-frequency knife as an example of the structure of a high-frequency knife of the fourth embodiment of the present invention, showing a state where the electrode knife is protruded from the distal end of the sheath.
Figure 13:
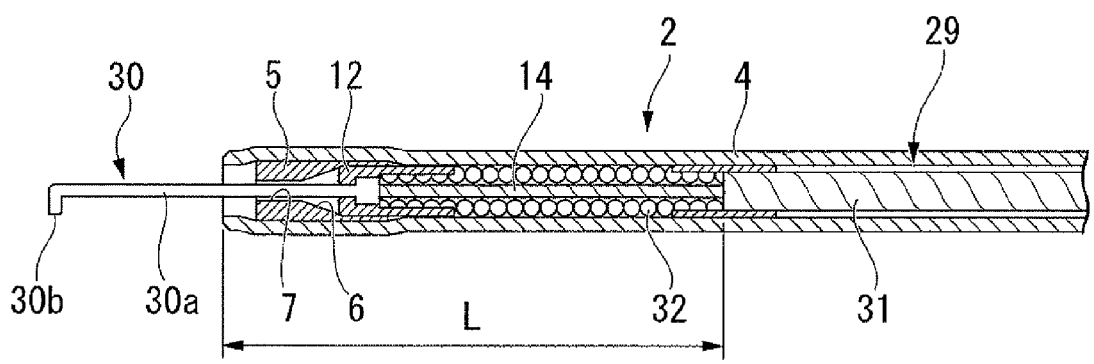
FIG. 13 is a partial cross-sectional view of the distal end portion of the high-frequency knife as an example of the structure of the high-frequency knife of the fourth embodiment of the present invention, showing a state in which the operating member is further compressed from the position at FIG. 12.
Figure 14A:
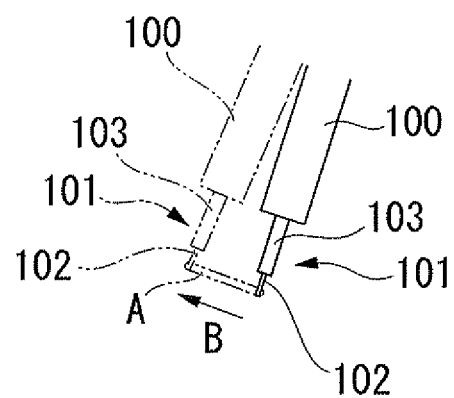
FIG. 14A is a view for showing a preferable incision and excision status of the target diseased site using the conventional high-frequency treatment tool.
Figure 14B:
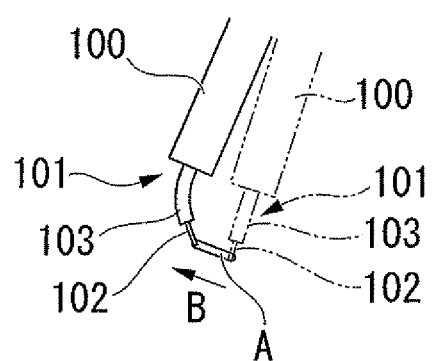
FIG. 14B is a view for showing deflection of the sheath when the conventional high-frequency treatment tool is used.

The coil sheath 32 may be a tightly wound coil as shown in FIG. 10 or may be a coil with each wire spaced as shown in FIG. 12. In this case, the length L is the length in which the wire is compressed and dense as shown in FIG. 13.

Furthermore, the operation of the fourth embodiment differs from the first embodiment in that only the coil sheath 32 which is disposed at the distal end of the sheath 2 is hardened when the operating slider 9 is further advanced with respect to the operator main body 8 from the position where the electrode knife 30 is protruded from the distal end of the sheath 2 and the operating member 29 is compressed. Therefore, in this embodiment, only the distal end of the sheath 2 is hardened. Other operations are the same as other embodiments. In this embodiment, since only the distal end of sheath 2 is hardened in the compressed status, the curving mechanism of the endoscope 16 is not affected.

As described above, according to each embodiment, the operating member provided with a treatment section which protrudes and retracts from the sheath at the distal end thereof is inserted to the flexible sheath so as to freely advance and retract. The operating member is formed of a member which has a characteristic of increasing the rigidity by compression, and the treatment tool includes a member which compresses the operating member. Therefore the electrode (treatment section) is protruded from the distal end of the sheath, and is used for incision or excision (treatment) by moving around the target treatment portion, a deflection can be prevented by increasing the rigidity due to compressing the operating member. Therefore sufficient incision or excision (treatment) can be achieved relative to the distance of movement.

While preferred embodiments of the invention have been described and illustrated above, it should be understood that these are exemplary of the invention and are not to be considered as limiting. Additions, omissions, substitutions, and other modifications can be made without departing from the spirit or scope of the invention. Accordingly, the invention is not to be considered as being limited by the foregoing description, and is only limited by the scope of the appended claims.

For instance, the shape of the edge of the electrode knife 15 of the high-frequency knife 1 is not limited to those illustrated in the figures in the first to the fourth embodiments.

Furthermore, in the embodiments above, although treatment tools which incise and excise by a transmitting high-frequency current are given as examples; the invention is not limited thereto, the tools may be non-high-frequency treatment tools such as dissection blades. The invention is also not limited to incising and excising tools, but may be any treatment tools used by protruding the treatment section from the sheath.

What is claimed is:

1. An endoscopic treatment tool comprising:
   a flexible sheath;
   an operating member inserted into the sheath so as to freely advance and retract in a longitudinal direction within the sheath;
   a treatment section disposed at a distal end of the operating member, the treatment section being configured to protrude and retract from the sheath by advancing and retracting the operating member;
   an operator section connected to a proximal end of the operating member, the operator section including a sliding member which freely advances and retracts relative to a main body of the operator section and makes the operating member advance and retract; and
   an abutting member disposed at a distal end of the sheath,
   wherein the operating member includes a first member which increases its rigidity by compression,
   a distal end of the first member is configured as a receiving portion which abuts the abutting member when the sliding member makes the operating member advance,
   the first member is configured to be compressed and to increase its rigidity by continuing to advance the sliding member in the longitudinal direction after the receiving portion abuts the abutting member,
   the treatment section is fixed to the distal end of the first member such that there is no relative motion between the treatment section and the distal end of the first member in the longitudinal direction, and
   the operating member and the abutting member are configured to prevent the distal end of the operating member and the treatment section from advancing so that a protrusion length of the treatment section from the sheath is set at a fixed length, when the sliding member continues to be advanced in the longitudinal direction after the receiving portion abuts the abutting member.

2. The endoscopic treatment tool according to claim 1, further comprising a second member which maintains a compressed status of the first member.

3. The endoscopic treatment tool according to claim 2, wherein the second member is disposed at the operator section.

4. The endoscopic treatment tool according to claim 3, wherein the second member prevents the sliding member of the operator section from retracting.

5. The endoscopic treatment tool according to claim 1, wherein the first member is a spring.

6. The endoscopic treatment tool according to claim 1, wherein the treatment section is able to penetrate through the abutting member, and the distal end of the operating member comes into contact with the abutting member so that the operating member is unable to penetrate through the abutting member.

7. The endoscopic treatment tool according to claim 6, wherein the abutting member is formed annularly, and the distal end of the first member comes into contact with the abutting member coaxially.

8. The endoscopic treatment tool according to claim 6, wherein
   the abutting member is formed tubularly,
   an inner surface of the abutting member has a tapered portion with reduced diameter toward the distal side of the sheath, and
   the distal end of the first member comes into contact with the tapered portion.

9. The endoscopic treatment tool according to claim 1, wherein:
   the endoscopic treatment tool is a high-frequency knife in which the treatment section is an electrode.

10. The endoscopic treatment tool according to claim 1, wherein the first member is formed in a coil shape.

11. The endoscopic treatment tool according to claim 1, wherein the operating member further includes an operating wire, and the first member is fixed to a distal end of the operating wire.

* * * * *